United States Patent [19]

Siegel et al.

[11] Patent Number: 5,296,636
[45] Date of Patent: Mar. 22, 1994

[54] PREPARATION OF 2,4,6-TRIMETHYLBENZOIC ACID

[75] Inventors: Wolfgang Siegel, Mannheim; Rudolf Kropp; Jochen Schroeder, both of Limburgerhof, all of Fed. Rep. of Germany

[73] Assignee: BASF Aktiengesellschaft, Ludwigshafen, Fed. Rep. of Germany

[21] Appl. No.: 10,058

[22] Filed: Jan. 28, 1993

[30] Foreign Application Priority Data

Jan. 30, 1992 [DE] Fed. Rep. of Germany ....... 4202567

[51] Int. Cl.$^5$ ...................... C07C 51/16; C07C 45/00
[52] U.S. Cl. ...................................... 568/323; 562/419
[58] Field of Search .......................... 562/419; 568/323

[56] References Cited

U.S. PATENT DOCUMENTS 3,530,189 9/1970 Moegeli ................................. 562/419
5,093,529 3/1992 Schmand ............................. 568/323

FOREIGN PATENT DOCUMENTS 0046194 2/1982 European Pat. Off. .
4000238 7/1991 Fed. Rep. of Germany .

OTHER PUBLICATIONS

Fuson, Chem. Rev., 15, pp. 275–309 (1964).
Allinger, "Organic Chemistry," pp. 497–499 (1971).
Bokova et al., "Chloroacetylation of Fluorene", J. Org. Chem., pp. 1103–1105 (1969).
Deposited Doc. (1976) Viniti 3747-76.
Deposited Doc., (1973) Viniti 7429-73.

Primary Examiner—Michael L. Shippen
Attorney, Agent, or Firm—Keil & Weinkauf

[57] ABSTRACT

A process for the preparation of 2,4,6-trimethylbenzoic acid of the formula I

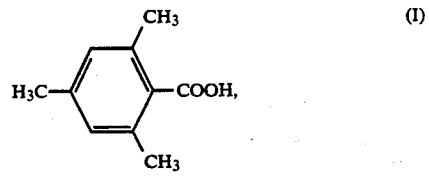

in which α-chloro-2,4,6-trimethylacetophenone is reacted with an alkali hydroxide solution and chlorine in the presence of a phase-transfer catalyst at a temperature ranging from 0° to 150° C. and a pressure ranging from 0.01 to 50 bar, and a process for the preparation of 2,4,6-trimethylbenzoic acid I, in which α-chloro-2,4,6-trimethylacetophenone of the formula II

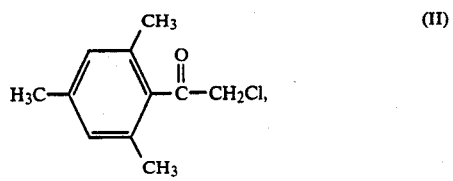

is reacted with 1,3,5-trimethylbenzene and chloroacetyl chloride in the presence of a catalyst at a temperature ranging from 0° to 150° C. and a pressure ranging from 0.01 to 50 bar, the catalyst used being an iron oxide.

4 Claims, No Drawings

PREPARATION OF 2,4,6-TRIMETHYLBENZOIC ACID

The present invention relates to a process for the preparation of 2,4,6-trimethylbenzoic acid from α-chloro-2,4,6-trimethylacetophenone and to the preparation thereof from 1,3,5-trimethylbenzene.

EP-A 46,194 discloses that 2,4,6-trimethylbenzoic acid can be manufactured from 2,4,6-trimethylacetophenone by way of a haloform dissociation reaction. A drawback of the procedure described therein is the poor space-time yield achieved with commercial soda bleaching lye.

DE-A 4,000,238 discloses that 2,4,6-trimethylacetophenone can be prepared from 1,3,5-trimethylbenzene and acetyl chloride in the presence of aluminum chloride acting as catalyst. Drawbacks associated with this procedure include the necessary molar amount of aluminum trichloride and the twofold excess of 1,3,5-trimethylbenzene required.

It is known to use catalytic amounts of iron(III) compounds in Friedel-Crafts acylations using chloroacetyl chloride, e.g., from *J. Org. Chem*. USSR 5 (1969) 1103 for FeCl$_3$, from Deposited Doc. (1973) VINITI 6940-6973 for Fe$_2$(SO$_4$)$_3$, from Deposited Doc. (1976) VINITI 3747-3776 and Deposited Doc. (1973) VINITI 7429-7473 for iron acetonylacetonate and iron salicylate. A good yield of acylation product is attained, however, only when a two-to-fourfold excess of aromatic compound is used.

It is thus an object of the prevent invention to overcome the aforementioned disadvantages.

Accordingly, we have found a novel and improved process for the preparation of 2,4,6-trimethylbenzoic acid of the formula I

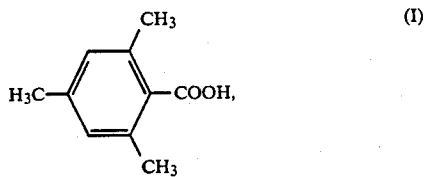

wherein α-chloro-2,4,6-trimethylacetophenone is reacted with an alkali hydroxide solution and chlorine in the presence of a phase-transfer catalyst at a temperature ranging from 0° to 150° C. and a pressure ranging from 0.01 to 50 bar and a process for the preparation of 2,4,6-trimethylbenzoic acid I, in which α-chloro-2,4,6-trimethylacetophenone of the formula II

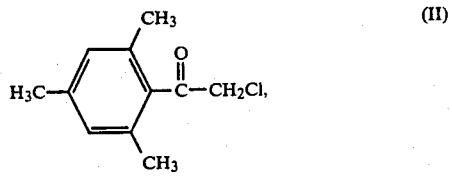

is reacted with 1,3,5-trimethylbenzene and chloroacetyl chloride in the presence of a catalyst at a temperature ranging from 0° to +150° C. and a pressure ranging from 0.01 to 50 bar, an iron oxide being used as catalyst.

The process of the invention may be carried out as follows:

α-Chloro-2,4,6-trimethylacetophenone II can be reacted in a haloform dissociation reaction with alkali metal hypochlorite solution produced in situ from an alkali hydroxide solution and chlorine at a temperature ranging from 0° to 150° C. and preferably from 30° to 80° C. and more preferably from 40° to 70° C. and a pressure ranging from 0.01 to 50 bar and preferably from 0.1 to 5 bar and more preferably at standard pressure (atmospheric pressure) in the presence of a phase-transfer catalyst.

Suitable alkali metal hydroxides are lithium hydroxide, sodium hydroxide, potassium hydroxide, rubidium hydroxide and cesium hydroxide and preferably lithium hydroxide, sodium hydroxide and potassium hydroxide and more preferably sodium hydroxide and potassium hydroxide.

The molar ratio of alkali metal hypochlorite to α-chloro-2,4,6-trimethylacetophenone II can be varied within wide limits; it is usually from 0.8:1 to 50:1 and preferably from 1:1 to 20:1 and more preferably from 1.5:1 to 5:1.

Suitable phase-transfer catalysts are advantageously quaternary salts, in particular catalysts of the formula

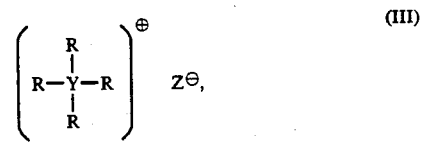

in which the individual radicals R may be the same or different and each denotes an aliphatic, cycloaliphatic, aromatic, or araliphatic radical, Y denotes a nitrogen, phosphorus, or arsenic atom, and Z stands for an acid anion. Preferred catalysts are those in the formulae of which the individual radicals R may be the same or different and each denotes an alkyl radical or an alkoxy group each having from 1 to 18 and preferably from 1 to 7 carbon atoms, a cycloalkyl radical having from 5 to 8 carbon atoms, an aralkyl radical or alkylaryl radical having from 7 to 12 carbon atoms, or a phenyl radical.

Examples of suitable starting materials III are:
tetra(methyl, n-propyl, isopropyl, n-butyl, isobutyl, sec-butyl, tert-butyl, pentyl, hexyl, n-heptyl, octyl, nonyl, decyl, undecyl, or dodecyl)ammonium chloride;
tetra(β-hydroxyethyl)ammonium chloride,
tetra(ω-hydroxypropyl)ammonium chloride,
tetra(β-hydroxypropyl)ammonium chloride,
tetra(δ-hydroxybutyl)ammonium chloride,
tetra(ω-hydroxybutyl)ammonium chloride,
tetra(β-hydroxybutyl)ammonium chloride,
tetra(α,α-dimethyl-β-hydroxyethyl)ammonium chloride,
tetra(α-methyl-β-hydroxypropyl)ammonium chloride,
tetra(β,β-dimethyl-β-hydroxyethyl)ammonium chloride,
tetra(α-ethyl-β-hydroxyethyl)ammonium chloride,
tetra(α-methyl-ω-hydroxypropyl)ammonium chloride,
tetra(β-methyl-ω-hydroxypropyl)ammonium chloride,
tetra(β-hydroxypentyl)ammonium chloride,
tetra(ω-hydroxypentyl)ammonium chloride,
tetra(δ-hydroxypentyl)ammonium chloride,
tetra(ω-hydroxypentyl)ammonium chloride,
tetra(β-hydroxypentyl)ammonium chloride;
ammonium chlorides obtained by quaternary substitution to include the aforementioned substituents and/or phenyl, benzyl, cyclohexyl, tolyl, methylcyclohexyl, phenylethyl, phenylpropyl, or phenylbutyl groups on the nitrogen atom and derived, respectively, from aniline, benzylamine, o-, m-, and p-toluidines, tri(phenyl, benzyl, cyclohexyl, methylcyclohexyl, phenylethyl, phenylpropyl, and phenylbutyl)amines, and triphenylamines which are 2-, 3-, or 4-monosubstituted by methyl on each phenyl ring or 2,4-, 2,3-, 2,6-, 2,5-, 3,4- or 2,5-disubstituted by methyl on each phenyl ring, which may alternatively be ammonium chlorides having four of the aforementioned radicals, some or all of which may differ from each other, e.g., quaternary ammonium chlorides obtained, by substitution with methyl, from N,N-dimethylaniline, N-methyl-N,N-diethylamine, N,N-dicyclohexyl-N-methylamine, and N-methyl-N-ethyl-N-n-propylamine;
dimethylbenzyldodecylammonium chloride,
cetyltrimethylammonium chloride,
methyltriethylammonium chloride,
dimethyldiphenylammonium chloride,
trimethyl(o-tert-butylphenyl)ammonium chloride,
$\beta$-ethoxyethyldimethyllaurylammonium chloride,
triethyldodecylammonium chloride,
trimethyltridecylammonium chloride,
trimethyldiphenylmethylammonium chloride,
trimethyl-n-dodecylammonium chloride,
trimethyl-$\beta$-hydroxyethylammonium chloride,
n-propyl-trimethylammonium chloride,
isoamyltrimethylammonium chloride,
benzyldimethyl-n-octylammonium chloride,
benzyltrimethylammonium chloride,
benzyltriethylammonium chloride,
phenyltrimethylammonium chloride,
dimethyldodecylphenylammonium chloride,
trimethyl[phenyl-(1)-ethyl]ammonium chloride, and
trimethyl[phenyl-(2)-ethyl]ammonium chloride;
corresponding ammonium bromides;
homologous quaternary ammonium salts of inorganic or
organic monobasic or polybasic acids such as
hydrochloric acid, hydrobromic acid, hydriodic acid, perchloric acid, sulfuric acid, phosphoric acid, nitrous acid, nitric acid, carbonic acid; sulfonic acids such as benzenesulfonic acid and p-toluenesulfonic acid; boron-containing acids such as boric acid, borofluoric acid; aliphatic carboxylic acids such as chloroacetic acid, dichloroacetic acid, and trichloroacetic acid;
or appropriate mixtures thereof.
We prefer to use the ammonium salts of hydrochloric acid, sulfuric acid, phosphoric acid, p-toluenesulfonic acid, monochloroacetic acid, and dichloroacetic and trichloroacetic acids; or homologous phosphonium or arsenium salts having said substituents on the hetero atom and/or acid anion.

The molar ratio of phase-transfer catalyst to $\alpha$-chloro-2,4,6-trimethylacetophenone II can be varied within wide limits and is usually from 0.001:1 to 0.1:1 and preferably from 0.01:1 to 0.08:1 and more preferably from 0.02:1 to 0.05:1.

The reaction of 1,3,5-trimethylbenzene and chloroacetyl chloride can be carried out at a temperature ranging from 0° to 150° C. and preferably from 50° to 100° C. and more preferably from 70° to 90° C. and a pressure ranging from 0.01 to 50 bar and preferably from 0.1 to 5 bar and more preferably at standard pressure (atmospheric pressure) in the presence of from 0.0001 to 5 mol % and preferably from 0.001 to 2 mol % and more preferably from 0.05 to 0.5 mol % of an iron oxide, preferably iron(III) oxide, to act as catalyst.

The molar ratio of chloroacetyl chloride to 1,3,5-trimethylbenzene is usually from 0.8:1 to 5:1 and preferably from 0.9:1 to 2.5:1 and more preferably from 1:1 to 2:1.

The reaction can be carried out in the presence or absence of an inert solvent. Suitable inert solvents are aromatic solvents such as nitrobenzene and chlorobenzene, aliphatic solvents such as heptane, toluene, and benzene, chlorinated solvents such as methyl chloride, and mesitylene. We prefer to use chlorobenzene, heptane and mesitylene, especially chlorobenzene and mesitylene.

2,4,6-trimethylbenzoic acid I is a useful starting material for the manufacture of dyes, pesticides, pharmaceuticals, and photoinitiators. For example, the benzoyl chloride corresponding to compound I yields, on reaction with alkoxyphosphines, compounds which are very useful as photoinitiators.

For information on further applications, reference is made to the aforementioned publications and *Ullmanns Encyclopaedie der technischen Chemie*, Vol. 4, pp. 272 to 291.

EXAMPLES

EXAMPLE 1

240 g of 1,3,5-trimethylbenzene and 80 mg of iron(III) oxide and 240 mL of chlorobenzene are placed in a vessel and refluxed (at ca 120° C.). 230 g of chloroacetyl chloride are added over a period of one hour. Shortly afterwards, generation of Cl begins. Stirring is continued, after completion of said addition, for a further two hours until gas generation ceases. The resulting solution is passed, without further treatment, to the haloform dissociation reaction.

EXAMPLE 2

120 g of 1,3,5-trimethylbenzene and 40 mg of iron(III) oxide are placed in a vessel and heated to 80° C. 113 g of chloroacetyl chloride are added over a period of one hour. Following said addition, stirring is continued for a further four hours as long as hydrogen chloride gas is generated. The product is then passed, without further treatment, to the haloform dissociation reaction as described in Example 4.

EXAMPLE 3

500 g of soda bleaching lye (ca 13% of active chorine), 720 g of caustic soda solution (25% strength) and 4 g of dimethyldibenzylammonium chloride in the form of a 50% strength aqueous solution are placed in a vessel and heated to 50° C. 202 g of a solution of $\alpha$-chloro-2,4,6-trimethylacetophenone in chlorobenzene (Example 1) are then added. The system is cooled to keep the temperature at from 50° to 60° C. 66 g of chlorine gas are then introduced over a period of one hour. Following the addition of chlorine, refluxing (from 105° to 108° C.) is continued for a further five hours, the chlorobenzene being removed from the circuit via a water separator.

The yellow reaction solution is discharged after being cooled to room temperature and is adjusted to pH 2 with ca 200 mL of concentrated hydrochloric acid. The white suspension is removed by filtration and the precipitate washed twice with 250 mL of cold water each time and dried in a vacuum shelf dryer at 80° C. There are obtained 90.3 g (90%) 2,4,6-trimethylbenzoic acid (mp 155° C.).

EXAMPLE 4

500 g of soda bleaching lye (ca. 13% of active chlorine), 720 g of caustic soda solution (25% strength) and 4 g of dimethyldibenzylammonium chloride in the form of a 50% strength aqueous solution are placed in a vessel and heated at 50° C. There are then added 160 g of an effluent as formed in Example 2. The system is cooled to maintain the temperature at from 50° to 60° C. 66 g of chlorine gas are then introduced over a period of one hour. Following the addition of chlorine, heating is continued for a further five hours at the refluxing temperature (ca 105° to 108° C.).

The yellow reaction solution is discharged after being cooled to room temperature and is adjusted to pH 2 with ca 200 mL of concentrated hydrochloric acid. The white suspension is removed by filtration and the precipitate washed twice with 250 mL of cold water each time and dried in a vacuum shelf dryer at 80° C. There are obtained 123.8 g (87%) of 2,4,6-trimethylbenzoic acid (mp 155° C.).

We claim:

1. A process for the preparation of α-chloro-2,4,6-trimethylacetophenone of formula II

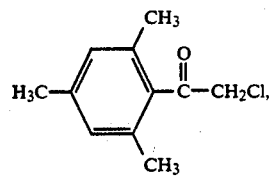

by the reaction of 1,3,5-trimethylbenzene with chloroacetyl chloride in the presence of a catalyst at a temperature ranging from 0° to +150° C. and a pressure ranging from 0.01 to 50 bar, wherein the catalyst used is an iron oxide.

2. A process for the preparation of α-chloro-2,4,6-trimethylacetophenone as define in claim 1 wherein the catalyst used is iron(III) oxide.

3. A process for the preparation of α-chloro-2,4,6-trimethylacetophenone as defined in claim 1 wherein 1,3,5-trimethylbenzene and chloroacetyl chloride are used in a molar ratio of from 0.3:1 to 3:1.

4. A process for the preparation of α-chloro-2,4,6-trimethylacetophenone as defined in claim 1 wherein 1,3,5-trimethylbenzene and chloroacetyl chloride are used in a molar ratio of from 0.8:1 to 1.2:1.

* * * * *